United States Patent
Eltorai et al.

(10) Patent No.: US 12,138,174 B2
(45) Date of Patent: Nov. 12, 2024

(54) IMPLANT FOR TOTAL WRIST REPLACEMENT

(71) Applicant: Orthopedix, Inc., Louisville, KY (US)

(72) Inventors: Adam E. M. Eltorai, Marlborough, MA (US); Ashok Seetharam, Louisville, KY (US); Vishal J. Thomas, Louisville, KY (US)

(73) Assignee: Mosaic Ventures, LLC, Marlborough, MA (US)

(*) Notice: Subject to any disclaimer, the term of this patent is extended or adjusted under 35 U.S.C. 154(b) by 0 days.

(21) Appl. No.: 17/521,637

(22) Filed: Nov. 8, 2021

(65) Prior Publication Data

US 2022/0062001 A1   Mar. 3, 2022

Related U.S. Application Data

(62) Division of application No. 16/045,737, filed on Jul. 26, 2018, now Pat. No. 11,166,822.

(Continued)

(51) Int. Cl.
*A61F 2/42* (2006.01)
*A61B 34/10* (2016.01)
*A61F 2/30* (2006.01)

(52) U.S. Cl.
CPC ............ *A61F 2/4261* (2013.01); *A61B 34/10* (2016.02); *A61F 2/30942* (2013.01); *A61B 2034/102* (2016.02); *A61F 2002/30604* (2013.01); *A61F 2002/30943* (2013.01); *A61F 2002/30948* (2013.01); *A61F 2002/4264* (2013.01);

(Continued)

(58) Field of Classification Search
None
See application file for complete search history.

(56) References Cited

U.S. PATENT DOCUMENTS 4,198,712 A  *  4/1980  Swanson ............... A61F 2/4261
                                                     623/21.14
4,645,505 A  *  2/1987  Swanson ............... A61F 2/4261
                                                      D24/155
(Continued)

FOREIGN PATENT DOCUMENTS

| CN | 1728976 A | * | 2/2006 | ......... A61F 2/30756 |
| GB | 2269752 A | * | 2/1994 | ........... A61F 2/4261 |
| WO | WO-2017120645 A1 | * | 7/2017 | |

*Primary Examiner* — Ann Schillinger
(74) *Attorney, Agent, or Firm* — Armis IP Law, LLC

(57) ABSTRACT

A surgical implant for total wrist replacement (TWR) includes a carpal portion and a radial portion to fully encompass both sides of the articulated joint defining wrist movement. The carpal portion is defined by a unitary structure that defines a fused form of the scaphoid, lunate and triquetrum, and bears against the radial portion for permitting articulated motion. The radial portion replaces a distal portion of the natural radius adjacent the wrist, and has the form of a "T" to combine a bearing surface with a stem adapted for implantation in the natural radius. The stem engages a receptacle or bore formed in a truncated end of the natural radius. Both the radial portion and the carpal portion patient-specific members are formed from image scans of the patient's own skeletal structures, and incorporate inverted, contralateral images of healthy structure based on an assessment of deformation in the replaced joint.

4 Claims, 5 Drawing Sheets

Related U.S. Application Data

(60) Provisional application No. 62/555,716, filed on Sep. 8, 2017.

(52) U.S. Cl.
CPC .......... *A61F 2002/4287* (2013.01); *A61F 2310/00029* (2013.01)

(56) References Cited

U.S. PATENT DOCUMENTS

| | | | |
|---|---|---|---|
| 5,458,646 A * | 10/1995 | Giachino | A61F 2/4261 623/21.12 |
| 6,090,145 A * | 7/2000 | Hassler | A61F 2/30721 623/23.14 |
| 6,436,146 B1 * | 8/2002 | Hassler | A61F 2/4261 623/18.11 |
| 6,746,486 B1 * | 6/2004 | Shultz | A61F 2/4261 623/21.12 |
| 7,531,003 B2 * | 5/2009 | Reindel | A61B 17/1659 623/21.12 |
| 7,837,739 B2 | 11/2010 | Ogilvie | |
| 7,918,894 B2 * | 4/2011 | Wolfe | A61F 2/4261 623/21.14 |
| 8,066,777 B2 * | 11/2011 | Palmer | A61F 2/4261 623/21.14 |
| 8,105,390 B2 * | 1/2012 | Shultz | A61F 2/4261 623/21.12 |
| D655,008 S | 2/2012 | Gannoe et al. | |
| 8,372,154 B2 * | 2/2013 | Schultz | A61F 2/4261 623/21.12 |
| 8,843,229 B2 | 9/2014 | Vanasse et al. | |
| 9,119,613 B2 | 9/2015 | Gannoe et al. | |
| 9,456,902 B2 * | 10/2016 | Hacking | A61F 2/30942 |
| 10,918,488 B2 * | 2/2021 | Eltorai | G06F 30/20 |
| 10,925,746 B2 * | 2/2021 | Eltorai | A61F 2/30942 |
| 11,166,822 B2 * | 11/2021 | Eltorai | A61F 2/4261 |
| 2006/0030946 A1 * | 2/2006 | Ball | A61F 2/4261 623/21.13 |
| 2009/0254190 A1 | 10/2009 | Gannoe et al. | |
| 2010/0087879 A1 * | 4/2010 | Vanasse | A61F 2/4261 606/86 R |
| 2011/0004317 A1 | 1/2011 | Hacking et al. | |
| 2011/0295378 A1 * | 12/2011 | Bojarski | A61F 2/30942 623/20.35 |
| 2014/0025181 A1 | 1/2014 | Vanasse et al. | |
| 2014/0358243 A1 * | 12/2014 | Saffar | A61F 2/4261 623/21.12 |
| 2014/0371863 A1 | 12/2014 | Vanasse et al. | |
| 2017/0143501 A1 * | 5/2017 | Honigmann | A61F 2/30942 |
| 2019/0201207 A1 * | 7/2019 | Giusti | A61F 2/0811 |

* cited by examiner

IMPLANT FOR TOTAL WRIST REPLACEMENT

RELATED APPLICATIONS

This application is a divisional application of earlier filed U.S. patent application Ser. No. 16/045,737 entitled "IMPLANT FOR TOTAL WRIST REPLACEMENT," filed on Jul. 26, 2018, which claims the benefit under 35 U.S.C. § 119(e) of U.S. Provisional Patent App. No. 62/555,716, filed Sep. 8, 2017, entitled "PATIENT-SPECIFIC TOTAL WRIST REPLACEMENT," the entire teachings of which are incorporated herein by this reference.

BACKGROUND

Prosthetic appliances are surgical implants that replace natural skeletal structures in a patient. Natural skeletal structures such as bones, tendons and ligaments can be compromised by age, disease and traumatic injury, as well as other causes. Surgical replacement with an orthopedic implant attempts to duplicate the original bone or skeletal member so that the patient may continue to enjoy mobility and dexterity once provided by healthy skeletal members. Replacement orthopedic implants are particularly beneficial in the wrist, as the natural skeletal structures include an arrangement of small, interconnected bones having specific irregular shapes that mesh and cooperate with other adjacent bones. Modern developments in CAD/CAM (computer aided design/computer aided manufacturing) has facilitated fabrication of these complex shapes.

Since the wrist is not a single-axis joint with collateral ligaments guiding a unidirectional arc of motion, the unconstrained wrist seldom rotates in a pure flexion-extension or radial-ulnar deviation mode, due to multiple degrees of freedom. In fact, most activities of daily living (using a hammer, fishing, bouncing a ball, or lifting heavy objects) involve an oblique type of wrist motion, from extension-radial deviation to flexion-ulnar deviation; it is the so-called "dart-throwing" plane of motion.

The human wrist helps to place the hand in optimal positions to perform a variety of tasks. For this reason, it is vital for hand function. When the wrist is degraded by disease or injury, hand function is compromised. As the wrist is a complex collection of multiple articulations, its anatomy and function is also complex.

SUMMARY

A surgical implant for total wrist replacement (TWR) includes a carpal portion and a radial portion to fully encompass both sides of the articulated joint defining wrist movement. The carpal portion is defined by a unitary structure that defines a fused form of the scaphoid, lunate and triquetrum, known as the Proximal Carpal Row (PCR), and bears against the radial portion for permitting articulated motion. The radial portion replaces a distal portion of the natural radius adjacent the wrist, and has the form of a "T" to combine a bearing surface with a stem adapted for implantation in the natural radius. The stem engages a receptacle or bore formed in a truncated end of the natural radius, and is embedded to a depth providing ample retention strength in response to patient wrist movement. Both the radial portion and the carpal portion are patient-specific members formed from image scans of the patient's own skeletal structures, and incorporate inverted, contralateral images of healthy structures based on an assessment of deformation or disease in the replaced joint.

Configurations herein are based, in part, on the observation that prosthetic surgical implants for human wrist replacement are required to bear substantial, complex loads from articulated movement that the prosthetic joint is expected to endure. Unfortunately, conventional approaches to total wrist replacement procedures suffer from the shortcoming of erosion and compromise at attachment points to the natural skeletal structures, particularly at the carpal component where screws and fasteners are typically employed for metacarpal attachment. The artificial prosthetics are mass-produced in a limited range of sizes, and have varying degrees of stability and attachment to the natural structures because of the need to be adaptable to a broad range of patients. Accordingly, configurations herein substantially overcome the above-described shortcomings by providing a TWR replacement prosthetic joint (implant) based on the specific patient anatomy it is replacing. A carpal component emulates the natural scaphoid, lunate and triquetrum as a single fused structure that is positionally retained by adjacent structures (bones), rather than via screws or rigid fasteners. A radial portion emulates a bearing surface from a scan of the natural radius it is replacing, and therefore engages with the natural structure of the emulated proximal carpal row (PCR). To accommodate anatomical degradation of the natural structures resulting from injury or disease, a contralateral scan from a healthy side (right or left) is employed and transposed to reflect the natural anatomy in the implant.

The disclosed method of fabricating a surgical implant therefore includes receiving a scanned image of a proximal carpal row (PCR), in which the PCR scan is based on imaging skeletal structures including a scaphoid, lunate and triquetrum of a patient anatomy, and receiving a scanned image of a distal portion of a radius of the patient adjacent the PCR. A fabrication system or mechanism generates a unitary carpal implant based on the received PCR scan, which is based on a fused representation of the imaged skeletal structures aggregated as a single solid shape. The fabrication system generates a radial implant based on the received radial scan, such that the radial implant has a bearing portion and an insertion portion arranged in a substantially perpendicular orientation. The insertion portion defines a stem engageable with a surgical recess or bore formed in a truncated radius of the patient and having a length corresponding to a depth of the surgical recess, in which the bearing portion has an underside adapted for abutting the truncated surface and a bearing surface for engaging the radial implant.

BRIEF DESCRIPTION OF THE DRAWINGS

The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

Depicted below is an example of a surgical implant fabrication and corresponding implantation procedure that fabricates the articulated wrist joint by corresponding carpal and radial implants based on patient-specific, contralateral scans of healthy bone, rather than mass-produced models designed to be screwed into existing bone structures. The disclosed implant includes a two part design for mated radial and carpal portions engaging via a bearing surface based on the patient's own anatomy. The prosthesis construction includes metal and/or polymer non-constrained materials. The radial component is made of alloys such as cobalt-chromium-molybdenum with surface texture for osseointegration. The carpal component is an ultra-high molecular weight polyethylene bearing surface or other polymer with a durable articulating surface for engaging the radial component, and is adapted for resilient tethered attachment rather than fixed screws or pins.

Figure 1:
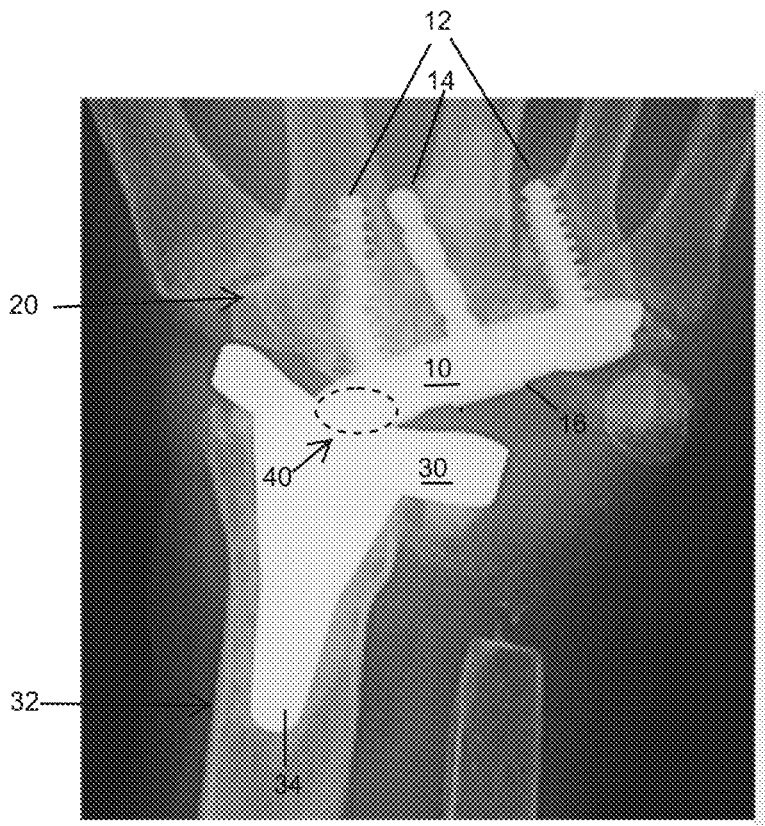
FIG. 1 shows a prior art implant.

FIG. 1 shows a prior art implant. In conventional implants, a carpal replacement 10 includes an array of threaded screws 12 and/or pins 14 for rigid, fixed attachment to existing wrist structures 20. The carpal replacement 10 joins with a replacement radius 30 attached to the natural radius bone 32 with a protrusion 34. An articulation region 40 defined by engagement and movement of the carpal replacement 10 in contact with the replacement radius 30 is prone to substantial force and wear because the surfaces are mass-produced artificial joints having a similar shape regardless of patient anatomy.

Figure 2:
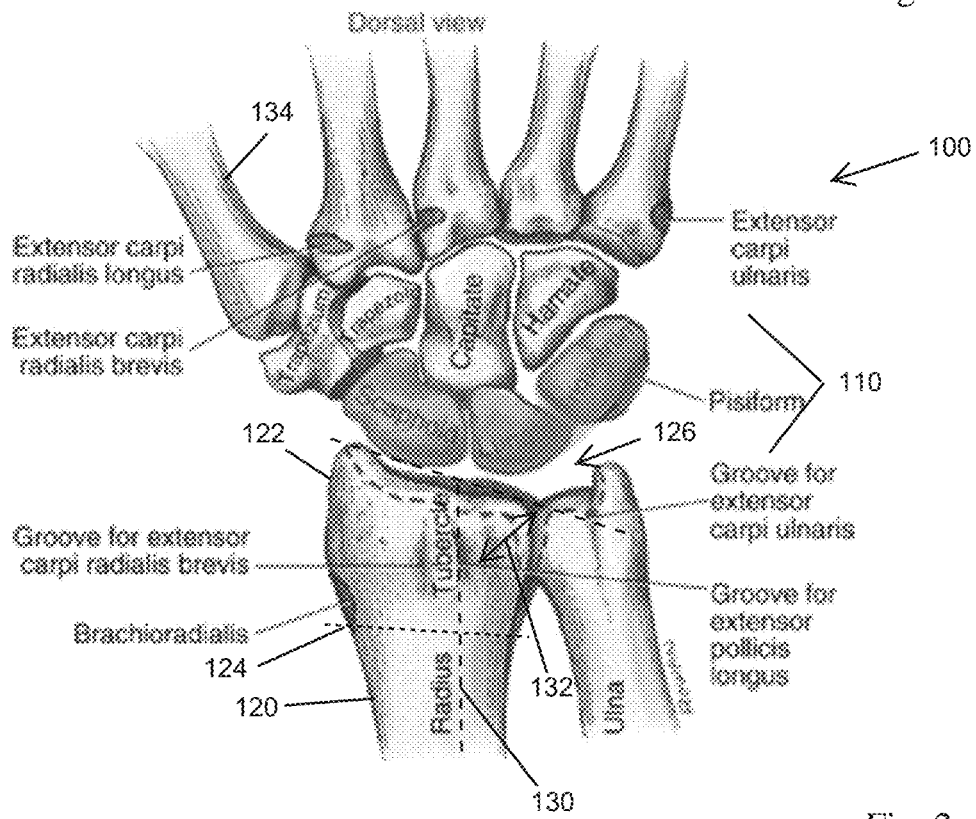
FIG. 2 is an anatomical diagram of a wrist suitable for depicting usage of the approach disclosed herein.

FIG. 2 is an anatomical diagram of a wrist suitable for depicting usage of the approach disclosed herein. Referring to FIG. 2, in a patient wrist anatomy 100, a proximate carpal row (PCR) 110 includes the three bones immediately adjacent to the radius: scaphoid, lunate and triquetrum. These bones take an intercalary placement, meaning that they are generally retained by adjacent bones, rather than directly by tendons or ligaments. In the claimed approach, a unitary carpal implant based on a fused representation of the PCR aggregated as a single solid shape is generated, similar to that disclosed in co-pending U.S. patent application Ser. No. 15/602,501, filed May 23, 2017, entitled "INTERCARPAL SURGICAL IMPLANT" and incorporated herein by reference in entirety.

A radial implant is based on a truncated radius 120, and replaces a truncated portion 122 distal of a truncation line 124 which includes a bearing surface 126 adjacent the PCR 110. The bearing surface 126 approaches the PCR 110 at an angle substantially perpendicular to a longitudinal axis 130 through the radius 120, deviating slightly based on a pre-operative angle 132 toward the thumb 134.

Image scans of the preoperative PCR 110 and truncated portion 122 provide anatomical detail for implant fabrication. Image scans of contralateral skeletal members may be employed if disease or injury compromises a beneficial or accurate scan of the afflicted members. Contralateral scans, upon inversion, closely approximate an anatomical equivalent of the patient's own anatomy of the healthy bone structures.

Figure 3:
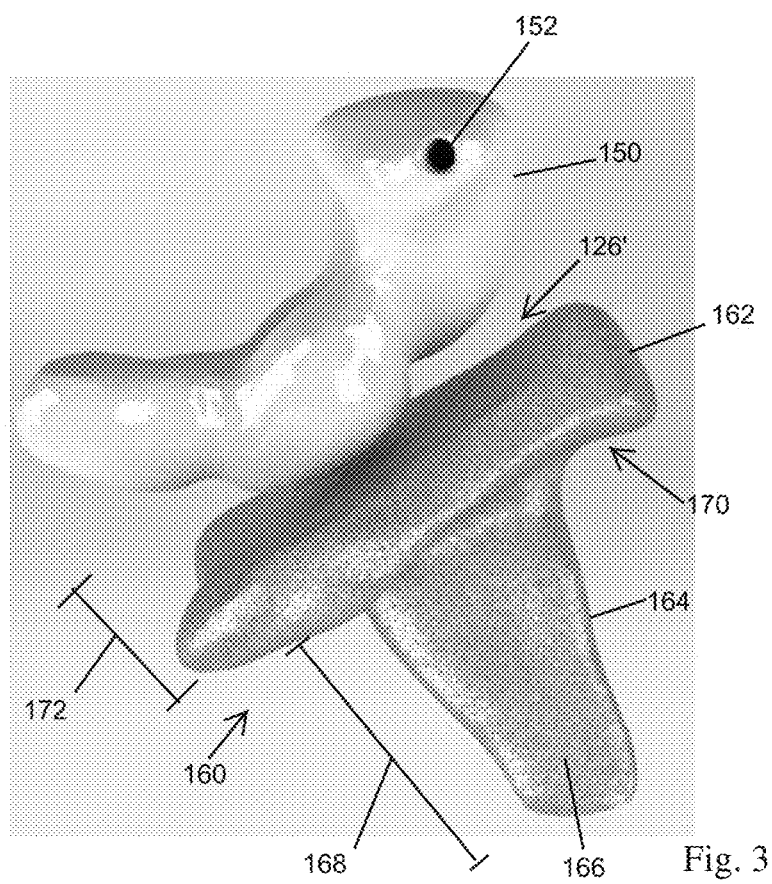
FIG. 3 is a perspective view of the implant as disclosed herein.

FIG. 3 is a perspective view of the implant as disclosed herein. Referring to FIGS. 2 and 3, the method of fabricating a surgical implant for TWR includes receiving a scanned image of the PCR 110, such that the scan is based on imaging skeletal structures including a scaphoid, lunate and triquetrum of a patient anatomy. Next, a scanned image of a distal portion of a radius of the patient is received, such that the distal portion is adjacent the PCR, and representing a diseased bone region or region to be replaced by the radial implant. A fabrication technique is employed to generating a unitary carpal implant based on the received PCR scan, such that the PCR implant depicts a fused representation of the imaged skeletal structures aggregated as a single solid shape. This unitary, solid shape is formed by applying a circumferential contour processing technique and a smoothing filter to the generated models of the PCR bones, such as by so-called "shrink wrap" effects, as if a planar sheet was tightly wrapped around the PCR bones.

A similar fabrication is employed for generating a radial implant 160 based on the received radial scan, such that the radial implant has a bearing portion 162 and an insertion portion 164 arranged in a substantially perpendicular orientation. The insertion portion 164 defines a stem 166 engageable with a surgical recess formed in the truncated radius 120 of the patient and having a length 168 corresponding to a depth of the surgical recess, shown further below in FIGS. 4 and 5. The bearing portion 162 has an underside 170 adapted for abutting the truncated surface of the natural radius 120 and a bearing surface for engaging the radial implant, defined by the truncation line 124.

The bearing portion 162 of the radial implant has a thickness 172 based on the truncation for approximating a preoperative length of the radius 120. Therefore, the effective length added by the thickness 172 will approximate and replace the length lost due to removed bone material. The substantially perpendicular orientation of the stem 166, along with thickness variations in the thickness, is based on the bearing (preoperative) angle 132 of the preoperative radius 120 relative to the longitudinal axis 130 of the radius.

Figure 4A:
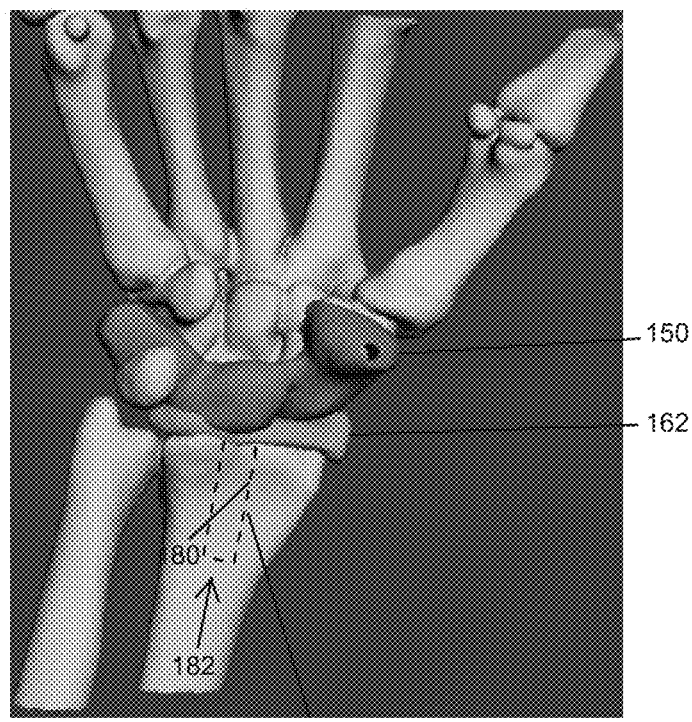
FIGS. 4a and 4b show dorsal and ventral views of the post surgical implant in a patient.
Figure 4B:
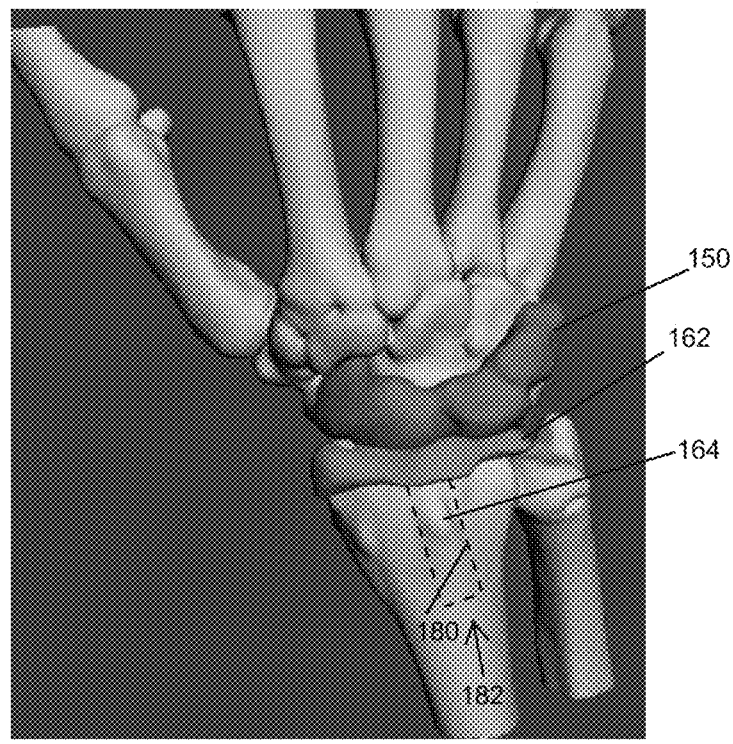

FIGS. 4a and 4b show dorsal and ventral views of the post surgical implant in a patient. Referring to FIGS. 3, 4a and 4b, the carpal implant 150 may employ a surgical tunnel 152 for tethered attachment of a suture or other fixation member. Formation, such as by drilling, molding, or defined voids in a 3D printing definition, provide the surgical attachment tunnel through the carpal portion adapted for receiving a surgical tether. Alternatively, the carpal implant 150 may maintain an intercalary positioning by relying on adjacent structures. Since the proximal row is an intercalary segment, the PCR replacement need not be implanted into any bone, nor rigidly attached to any structure. This feature removes the need for intra-medullary fixation and osseo-integration of the implant. Surgical anchors, discussed further below, may also be employed.

In the implant of FIGS. 4a and 4b, the stem 164 has a radial dimension (i.e. radius or thickness) based on anticipated bearing forces on the radial implant 160, which would be transferred to interior walls 180 of the surgical recess 182. The surgical recess 182 may be formed in the natural radius 120 at the truncation line 124 as a drilled bore corresponding to the insertion depth 168, or other suitable implantation technique.

Either the radial or carpal implants may employ contralateral imaging for supplementing or replacing deficiencies or degradation of the preoperative structures to be replaced, as a reliable approximation is obtainable from the corresponding structure on the opposed side (right or left). This provides the benefits of the patient's own anatomical structure over an artificial replacement, event when the original structure has been compromised due to disease or injury. Fabrication of either of the implants may employ respective contralateral images for the PCR scan and the radial scan, or both. Therefore, at least one of the radial and carpal implants may be based on a contralateral, inverted image of a healthy skeletal structure of the patient.

Figure 5:
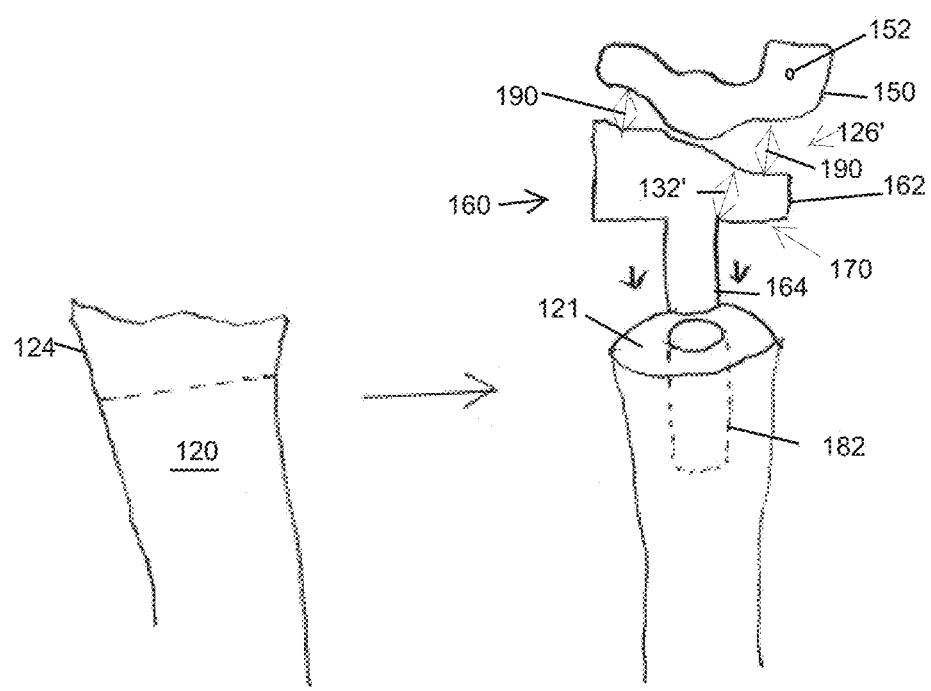
FIG. 5 is a pre-implantation view of the implant of FIGS. 3-4b.

FIG. 5 is a pre-implantation view of the implant of FIGS. 3-4b. Referring to FIGS. 3-5, a cut or excision of the radius 120 is made at the attachment line 124. The surgical recess 182 is defined by a bore or receptacle for engaging the stem 164 of the radial implant 160. The underside 170 of the implant 160 rests on the radius 120 on a shoulder 121 defined by the excision. An implant bearing surface 126' abuts the PCR implant 150, and, based on the thickness 172 and the shoulder 121, approximates the preoperative angle 132, as shown by arrow 132'. The PCR implant 150 is therefore permitted articulated movement against the bearing surface 126', as shown by arrows 190.

Figure 6A:
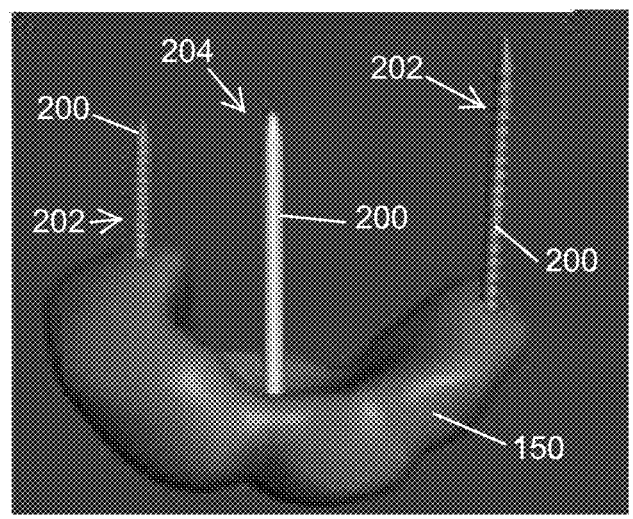
FIG. 6a shows a side view of inserted anchors in the implant of FIGS. 3-4b.
Figure 6B:
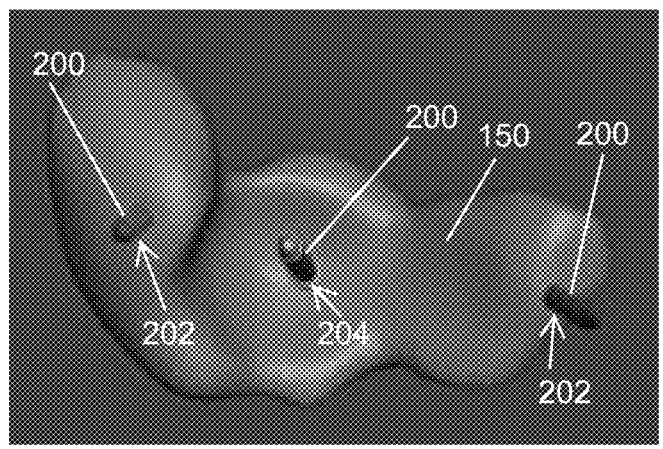
FIG. 6b shows a view of the implant from the anchor insertion perspective.

FIG. 6a shows a side view of inserted anchors in the implant of FIGS. 3-4b. Referring to FIGS. 3 and 6a, anchors 200. The anchors generally include an elongated cylindrical surface, and may include threads 202, a smooth surface 204, and may be tapered or continuous. FIG. 6b shows a view of the implant from the anchor insertion perspective prior to implantation. Any suitable bone or surgical anchor may be employed, and may be formed with the implant 150 or inserted post-formation.

Figure 6C:
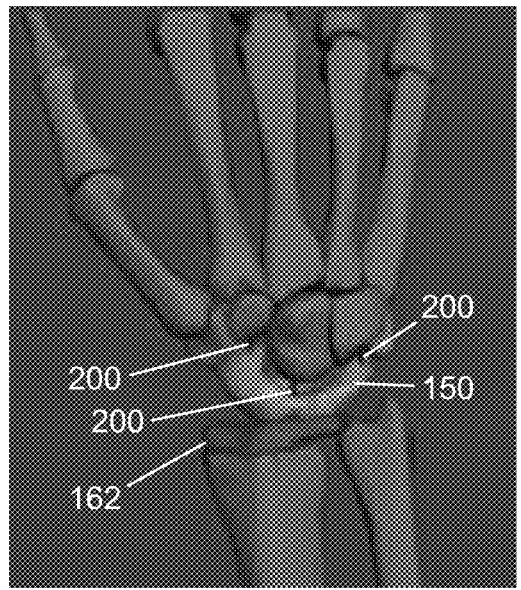
FIG. 6c shows the anchored implant.
Figure 6D:
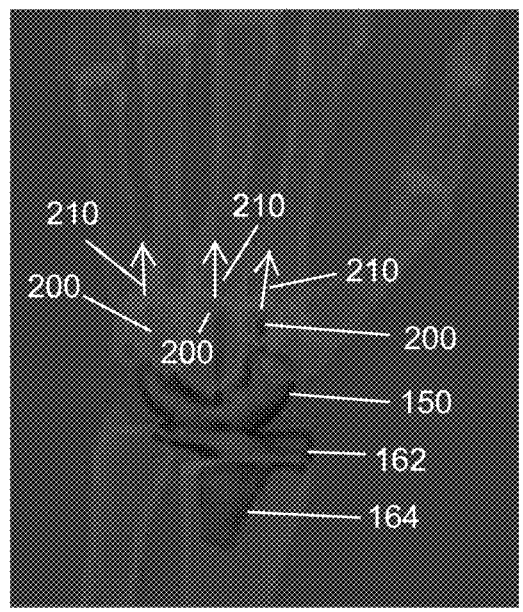
FIG. 6d shows the anchored implant from an alternate view.

FIG. 6c shows the anchored implant secured to adjacent bones via the anchors 200. Holes may be drilled or formed in the existing structures for defining a receptacle for the anchors. FIG. 6d shows the anchored implant from an alternate view depicting the existing structures in a transparent mode. The anchors 200 extend into the existing structures and abut the bearing portion 162 on an opposed side, where the stem 164 secures the bearing portion 162. An inserted trajectory 210 of the anchors 200 is shown. The anchors retaining and position the carpal component of the implant using 3 bone screws, and further orient screw bores such that they are angled and drilled according to the existing structures of the patient's anatomy. The preexisting bone structures may have compromised or thin portions. Orientation of the anchors 200 allows the anchors to penetrate in areas of maximum strength and resistance to failure and pullout.

Figure 6E:
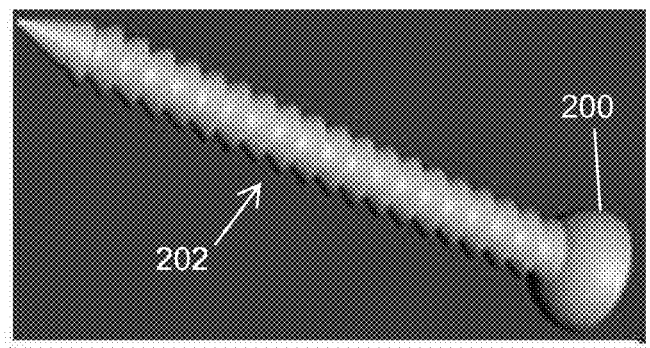
FIG. 6e shows an anchor for securing the implant of FIGS. 6a-d.
Figure 6F:
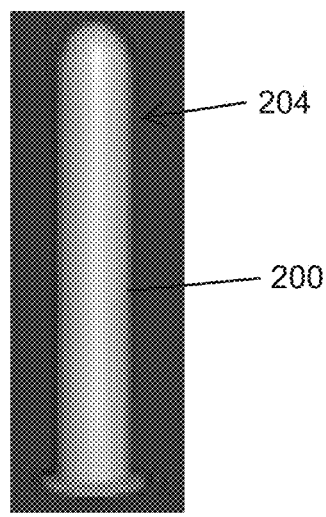
FIG. 6f shows an alternate anchor.

FIG. 6e shows an anchor for securing the implant of FIGS. 6a-d. Referring to FIGS. 6a-6f, the anchor 200 defines a generally elongated member having a cylindrical shape adapted for frictional securement in a skeletal member. The anchor 200 may have a threaded surface 202, adapted for rotary insertion, or may have a smooth or flush surface 400, adapted for forced insertion, as in FIG. 6f.

Those skilled in the art should readily appreciate that the programs and methods defined herein are deliverable to a user processing and rendering device in many forms, including but not limited to a) information permanently stored on non-writeable storage media such as ROM devices, b) information alterably stored on writable non-transitory storage media such as floppy disks, magnetic tapes, CDs, RAM devices, and other magnetic and optical media, or c) information conveyed to a computer through communication media, as in an electronic network such as the Internet or telephone modem lines. The operations and methods may be implemented in a software executable object or as a set of encoded instructions for execution by a processor responsive to the instructions. Alternatively, the operations and methods disclosed herein may be embodied in whole or in part using hardware components, such as Application Specific Integrated Circuits (ASICs), Field Programmable Gate Arrays (FPGAs), state machines, controllers or other hardware components or devices, or a combination of hardware, software, and firmware components.

While the system and methods defined herein have been particularly shown and described with references to embodiments thereof, it will be understood by those skilled in the art that various changes in form and details may be made therein without departing from the scope of the invention encompassed by the appended claims.

What is claimed is:

1. A surgical implant assembly, comprising:
   a unitary carpal implant based on a received proximal carpal row (PCR) scan, the implant based on a fused and wrapped representation of the imaged skeletal structures including a scaphoid, lunate and triquetrum aggregated as a single solid shape, the implant further based on a contralateral, inverted image of a corresponding healthy skeletal structure of a patient anatomy;
   a radial implant based on a received radial scan, the radial implant having a bearing portion and an insertion portion arranged in a substantially perpendicular orientation,
   the insertion portion defining a stem engageable with a surgical recess formed in a truncated radius of the patient and having a length corresponding to a depth of the surgical recess; and
   the bearing portion having an underside adapted for abutting the truncated surface and a bearing surface for engaging the radial implant and a thickness based on a preoperative length of the radius, thereby approximating the natural radius length via the bearing portion.

2. The implant of claim 1 wherein the substantially perpendicular orientation is based on a bearing angle of the preoperative radius relative to a longitudinal axis of the radius.

3. The implant of claim 1 wherein the thickness and an insertion depth of the radial implant are based on anticipated bearing forces on the radial implant and transferred to the truncated, natural radius.

4. The implant of claim 1 wherein the stem has a radial dimension based on anticipated bearing forces on the radial implant and transferred to interior walls of the surgical recess.

* * * * *